United States Patent [19]

Lockwood

[11] Patent Number: 4,491,129
[45] Date of Patent: Jan. 1, 1985

[54] STRAPPING ASSEMBLY AND METHOD FOR THE TREATMENT OF ACROMIOCLAVICULAR SEPARATIONS

[76] Inventor: Robert C. Lockwood, Stevens Rd., Marcellus, N.Y. 13108

[21] Appl. No.: 259,481

[22] Filed: Apr. 30, 1981

[51] Int. Cl.³ .............................................. A61F 5/40
[52] U.S. Cl. .................................................... 128/94
[58] Field of Search ..................... 128/94, 87 R, 87 B, 128/82, 68, 69, 80 G, 520, 426, DIG. 15; 3/15, 16; 2/44, 45, 310, 323, 335

[56] References Cited

U.S. PATENT DOCUMENTS

| | | | |
|---|---|---|---|
| 396,837 | 1/1899 | Shockey | 2/44 X |
| 636,562 | 11/1899 | Rouse | 2/44 X |
| 1,808,422 | 6/1931 | MacDonald | 128/94 |
| 3,404,680 | 10/1968 | Gutman et al. | 128/94 |
| 4,188,944 | 2/1980 | Augustyniak | 128/94 |

FOREIGN PATENT DOCUMENTS

| | | | |
|---|---|---|---|
| 889539 | 10/1943 | France | 128/87 |

Primary Examiner—Richard J. Apley
Assistant Examiner—David J. Brown
Attorney, Agent, or Firm—Bruns & Wall

[57] ABSTRACT

A strapping assembly and method for the treatment of acromioclavicular separations. The strapping assembly includes a stocking that is worn on the leg of the patient on the side opposite the injury and serves an an anchor. A tension member strap is connected to the stocking through an adjustable garter. From the stocking, the strap extends upwardly to the patient's shoulder on the side of the injury and then over the shoulder and downwardly to the patient's forearm. The strap is looped around the forearm to hold it sling fashion and the weight of the forearm places the strap under tension. After the strapping assembly has been applied to the patient, the acromioclavicular separation is reduced by the physician by closed reduction and then the tension on the tension member is adjusted to maintain the reduction.

1 Claim, 3 Drawing Figures

STRAPPING ASSEMBLY AND METHOD FOR THE TREATMENT OF ACROMIOCLAVICULAR SEPARATIONS

BACKGROUND OF THE INVENTION

This invention relates generally to medical and surgical appliances and methods, and has particular reference to a novel strapping assembly and method for the treatment of acromioclavicular separations.

There are at the present time a large number of operative and nonoperative methods of treating acromioclavicular separations. These are divided into three basic categories: open reduction with internal fixation, closed reduction with maintenance by strapping, and what is known as studied neglect. While open reduction and studied neglect can give good results, both have certain disadvantages. Thus, open reduction exposes the patient to operative apprehension, an unsightly scar and the possibility of complications. Studied neglect, on the other hand, may leave an unsatisfactory cosmetic result.

Closed reduction and strapping may give both acceptable functional and acceptable cosmetic results. However, certain closed reduction techniques cause skin maceration and ulceration, allow loss of reduction, and are too uncomfortable for prolonged use. There is therefore a need for a means to achieve normal shoulder function with a cosmetically acceptable appearance, and at a low cost.

SUMMARY OF THE INVENTION

The present invention satisfies the need expressed just above by providing an effective strapping assembly and a relatively low cost, nonoperative method for the treatment of acromioclavicular separations. With the equipment and method of the invention, it is possible to achieve both acceptable functional and acceptable cosmetic results without causing skin disorders or prolonged discomfort to the patient. In addition, the nonoperative approach of the invention spares the patient the possibility of psychological side effects or potential complications resulting from an operation.

The strapping assembly of the invention includes a high stocking that is worn on the leg of the patient on the side opposite the injury and serves as an anchor. A tension member in the form of an elongated strap is connected to the stocking through an adjustable garter. From the stocking, the strap extends upwardly across the patient's back to the shoulder on the side of the injury and then over the shoulder and downwardly to the patient's forearm. The strap is looped around the forearm to hold it sling fashion at substantially right angles to the upper arm. The weight of the forearm places the strap, anchored at its other end to the stocking, under tension.

After the strapping assembly has been applied to the patient as above described, the acromioclavicular separation is reduced by the physician by closed reduction. Thereafter, the tension on the tension member is adjusted by means of the garter to maintain the reduction.

DESCRIPTION OF THE PREFERRED EMBODIMENT

Figure 2:
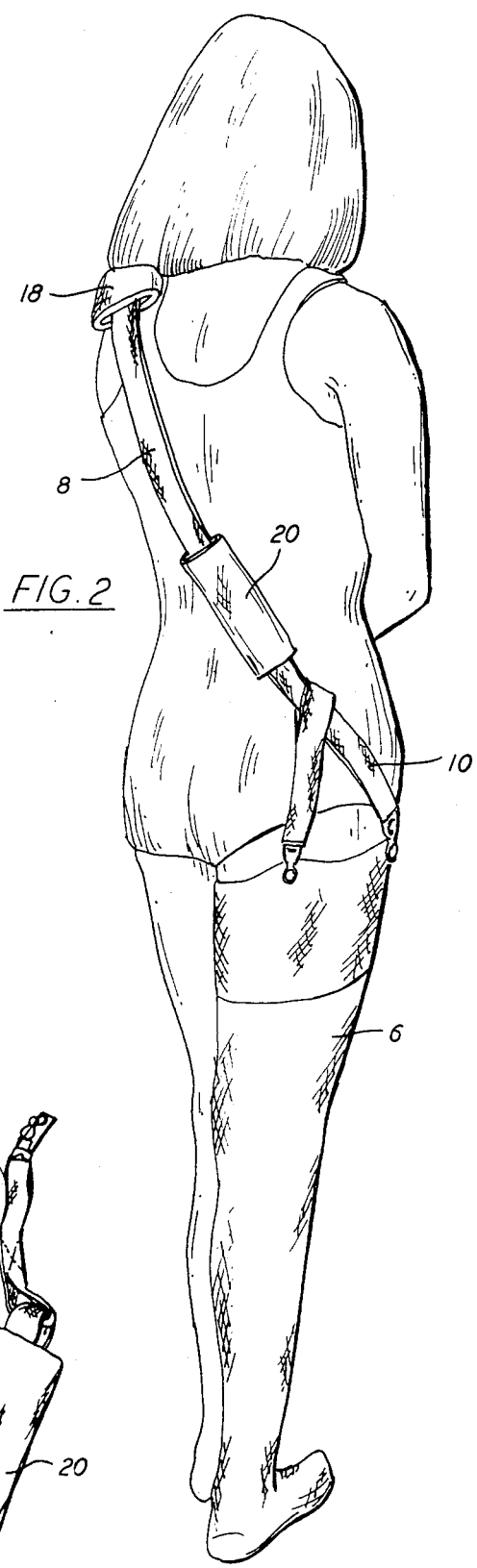
FIG. 2 is a back view of the patient and of the strapping assembly.
Figure 3:
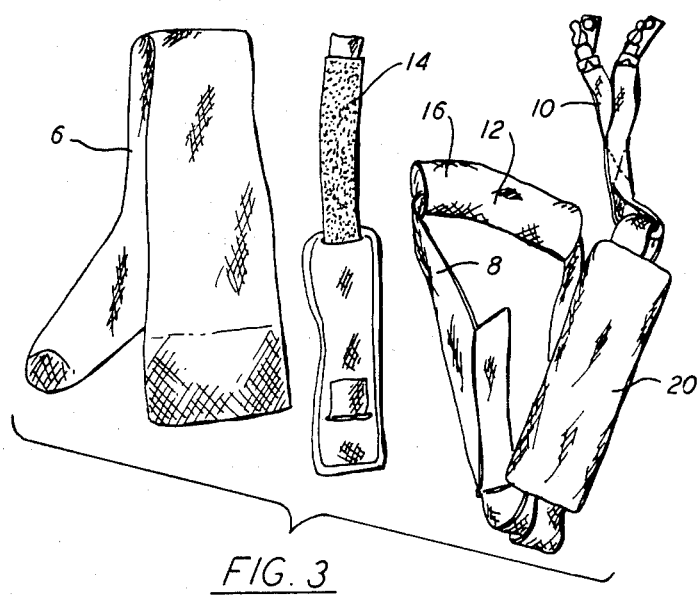
FIG. 3 is an exploded type view illustrating the components of the strapping assembly individually.

Having reference now to the drawings, the strapping assembly includes a high stocking 6 of strong construction which stocking is worn by the patient on the leg opposite the injury. In the illustrated application of the invention, it has been assumed that the acromioclavicular separation being treated is on the patient's left side (left clavicle) and therefore the stocking is worn on the right leg as shown. The stocking 6 serves as an anchor for a tension member in the form of a canvas strap 8, one end of this strap being connected to the stocking through an adjustable elastic garter 10, FIGS. 2 and 3.

Figure 1:
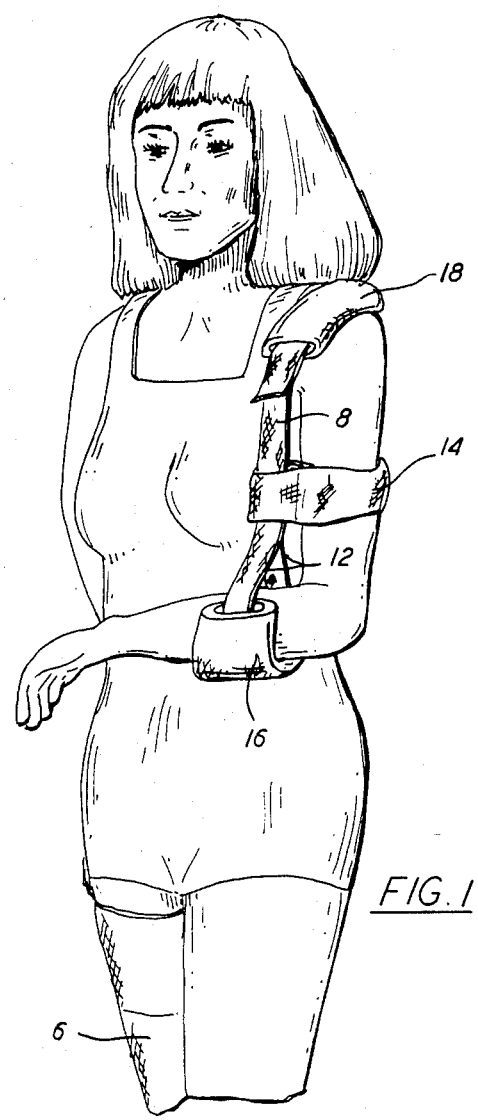
FIG. 1 is a fragmentary front view of a patient wearing the strapping assembly of the invention.

From the garter 10, the strap 8 extends upwardly across the back of the patient and passes over the left shoulder, the side of the injury. The strap then extends downwardly to the patient's left forearm, this end of the strap being formed into a loop 12 for supporting the forearm in sling fashion, or at approximately right angles to the upper arm as shown in FIG. 1. Suitable means (not shown) are provided for adjusting the height of the bottom of loop 12 and therefore adapt to the size and build of the particular patient.

A counter force band 14 of the type used in tennis and other racquet sports to combat "tennis elbow" is applied so as to loosely encircle the patient's upper arm and a portion of the strap 8 that is adjacent thereto. The band 14 operates to help hold the tension strap 8 in the desired position on the patient. The strapping assembly includes a plurality of felt pads to prevent skin irritation, pads 16, 18 and 20 being shown in contact with the patient's forearm, shoulder and back, respectively. Benzoin may be applied to the skin engaging sides of these pads.

After the strapping assembly has been applied to the patient as above described, the acromioclavicular separation is reduced by the physician by closed reduction. This is not accomplished by the assembly. Thereafter, the physician adjusts the tension on the strap 8 by means of the garter 10 to maintain the reduction in the desired manner.

The strapping assembly maintains the reduction in three basic ways. First, the anchoring of the strap 8 at the contralateral proximal thigh and very near the center of the flexion-extension of the elbow provides constant compression of the distal clavicle and elevation of the scapula even in the recumbent position. Second, in the erect position, the long lever arm accentuates the weight of the forearm to apply compression-elevation by virtue of gravitational forces. Third, the presence of a fulcrum on the ulnar provides for a dynamic element of maintenance of reduction with contraction of the triceps. The absence of a thoracic binder eliminates interference with respiration and a potential source of skin complications. The stocking 6 and garter 10 distribute the pressure evenly over the lower extremity and eliminate the bulky components at the groin and gluteal region, again reducing the chances of skin irritation.

From the foregoing description it will be apparent that the invention disclosed herein provides a novel and highly advantageous strapping assembly and method for the treatment of acromioclavicular separations. As will be understood by those familiar with the art, the invention may be embodied in other specific forms without departing from the spirit or essential charcteristics thereof.

I claim:

1. A strapping assembly for the treatment of an acromioclavicular separation comprising a high stocking worn on the leg of the patient on the side opposite the injury, an elongated strap member, an elastic garter connecting one end of the strap member to the top of the stocking, the garter being adjustable to enable the tension on the strap member to be adjusted after the latter has been positioned on the patient, the strap member being long enough to extend upwardly from the garter diagonally across the patient's back to the shoulder on the side of the injury and then over the shoulder and downwardly to the patient's forearm on the side of the injury, the strap member haveing an adjustable closed loop at its opposite end for encircling the forearm and supporting it in sling position, and an adjustable diameter band encircling the upper arm on the side of the injury and a portion of the strap member adjacent thereto, the band serving to help hold the strap member in proper position on the patient.

* * * * *